US006888629B1

(12) United States Patent
Boss et al.

(10) Patent No.: US 6,888,629 B1
(45) Date of Patent: May 3, 2005

(54) SENSOR FOR PERFORMING SURFACE ENHANCED RAMAN SPECTROSCOPY AND METHOD FOR ACHIEVING SAME

(75) Inventors: Pamela A. Boss, San Diego, CA (US); Stephen H. Lieberman, La Mesa, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 803 days.

(21) Appl. No.: 09/888,737

(22) Filed: Jun. 25, 2001

Related U.S. Application Data

(63) Continuation-in-part of application No. 09/805,665, filed on Mar. 13, 2001, now Pat. No. 6,614,523, and a continuation-in-part of application No. 09/593,675, filed on Jun. 14, 2000, now Pat. No. 6,406,777.

(51) Int. Cl.[7] .................................................. G01J 3/44

(52) U.S. Cl. ...................................................... 356/301

(58) Field of Search ................................ 356/300–309, 356/36–50; 600/315–323, 600

(56) References Cited

U.S. PATENT DOCUMENTS

| 5,010,776 A | 4/1991 | Lucero et al. |
|---|---|---|
| 5,112,127 A | 5/1992 | Carrabba et al. |

(Continued)

OTHER PUBLICATIONS

Storey, J. M. E. et al., "Electrochemical SERS Detection of Chlorinated Hydrocarbons in Aqueous Solutions", *Applied Spectroscopy*, vol. 48, No. 10, 1994.

Mullen, K. et al., "Adsorption of Chlorinated Ethylenes at 1–Octadecanethiol–Modified Silver Surfaces", *Analytical Chemistry*, vol. 66, No. 4, Feb. 15, 1994.

Schoen, C. L. et al., "Long fiber–optic remote Ramen probe for detection and identification of weak scatterers", *Applied Optics*, vol. 31, No. 36, Dec. 20, 1992.

Crane, L. G. et al., "SERS Surfaces Modified with a 4–(2–Pyridylazo) resorcinol Disulfide Derivative: Detection of Copper, Lead, and Cadmium", *Analytical Chemistry*, vol. 67, No. 2, Jan. 15, 1995.

Carron, K. T. et al., "Molecular–Specific Chromatographic Detector Using MOdified SERS Substrates", *Analytical Chemistry*, vol. 67, No. 18, Sep. 15, 1995.

Carron, K. et al., "Octadecylthiol–Modified Surface–Enhanced Raman Spectroscopy Substrates: A New Method for the Detection of Aromatic Compounds", Environ. Sci. Technol., vol. 26, No. 10, 1992.

Carrabba, M. M. et al., "Fiber Optic Raman Chemical Sensors", *Proceedings of the Sumposium on Chemical Sensors II*, vol. 93–7.

*Primary Examiner*—Tu T. Nguyen
(74) *Attorney, Agent, or Firm*—Andrew J. Cameron; Michael A. Kagan; Allan Y. Lee

(57) ABSTRACT

A sensor for performing surface enhanced Raman spectroscopy comprises: a) a sensor body having a throughbore; an optical energy source for generating an optical excitation signal; b) a surface enhanced Raman scattering structure that is mounted to the sensor body through which the optical excitation signal is directed for irradiating an analyte, whereupon the analyte generates primary Raman emissions in response to being irradiated by the optical excitation signal, and wherein the surface enhanced Raman scattering structure generates secondary Raman emissions when irradiated by the optical excitation signal; c) an optical detector for generating an output signal that represents the spectral characteristics of the primary and secondary Raman emissions in response to receiving the primary and second Raman emissions; and d) a processor for substantially filtering the secondary Raman emission from the primary Raman emissions and for generating an output signal representing the analyte.

8 Claims, 2 Drawing Sheets

U.S. PATENT DOCUMENTS

| | | |
|---|---|---|
| 5,194,913 A | 3/1993 | Myrick et al. |
| 5,241,368 A | 8/1993 | Ponstingl et al. |
| 5,376,556 A | 12/1994 | Tarcha et al. |
| 5,402,508 A | 3/1995 | O'Rourke et al. |
| 5,567,628 A * | 10/1996 | Tarcha et al. ............... 436/525 |
| 5,739,536 A | 4/1998 | Bucholtz et al. |
| 5,759,859 A | 6/1998 | Sausa |
| 5,774,610 A | 6/1998 | O'Rourke et al. |
| 6,018,389 A | 1/2000 | Kyle et al. |
| 6,028,666 A | 2/2000 | Boss et al. |
| 6,222,970 B1 * | 4/2001 | Wach et al. ................. 385/115 |
| 6,226,082 B1 * | 5/2001 | Roe ........................... 356/301 |

* cited by examiner

SENSOR FOR PERFORMING SURFACE ENHANCED RAMAN SPECTROSCOPY AND METHOD FOR ACHIEVING SAME

CROSS REFERENCE TO RELATED APPLICATIONS

This application is a continuation-in-part of commonly assigned U.S. patent application Ser. No. 09/593,675, filed 14 Jun. 2000, now U.S. Pat. No. 6,406,777 and entitled A METAL AND GLASS STRUCTURE FOR USE IN SURFACE ENHANCED RAMAN SPECTROSCOPY AND METHOD FOR FABRICATING SAME, and is a continuation-in-part of commonly assigned U.S. patent application Ser. No. 09/805,665, filed 13 Mar. 2001, now U.S. Pat. No. 6,614,523 and entitled SENSOR FOR PERFORMING SURFACE ENHANCED RAMAN SPECTROSCOPY.

BACKGROUND OF THE INVENTION

The present invention generally relates to the field of Raman spectroscopy, and more particularly, to a sensor for detecting chemicals both in gas and liquid environments using surface enhanced Raman spectroscopy in which any Raman scattering due to excitation of the optical elements of the sensor are minimized.

Raman spectroscopy is an emission technique that involves inelastic scattering of incident laser energy and results in spectral peaks that are frequency shifted from the incident energy. The Raman bands arise from changes in polarizability in a molecule during vibration. As a result, virtually all organic molecules display a characteristic Raman emission. Therefore, a Raman sensor would not be limited to a specific class of molecules as is the case for the laser induced fluorescence (LIF) sensor. Raman spectrometry allows the fingerprinting of species present and is structurally specific. The inherently high resolution of Raman spectra often permits the analysis of several components in a mixture simultaneously.

The advent of inexpensive, portable Raman spectrometers has seen renewed interest in the area of Raman spectrometry. This new generation of spectrometers employs fiber-optic probes, holographic notch filters for rejection of the Rayleigh line, a single grating monochromator, and a charge-coupled device (CCD) detector for multichannel detection. These spectrometers contain a minimum of optical components as compared to conventional Raman instrumentation resulting in high throughputs; and, once coupled to a laser and spectrometer, optical-fiber probes require no further alignment.

Despite the advantages of Raman spectroscopy over other spectroscopic techniques and the technological advances in the area of Raman spectrometry, Raman spectroscopy is, inherently, an insensitive technique. To achieve detection limits in the low ppm range would require either the use of a multiple pass cell or long acquisition times. In the 1970s, it was discovered that Raman scattering from molecules adsorbed on such noble metals as silver, copper, and gold can be enhanced by as much as $10^6$ to $10^7$. This phenomenon, called surface enhanced Raman spectroscopy (SERS), is still not understood despite intensive theoretical and experimental research. It is believed that more than one mechanism is involved in the SERS phenomenon. Initially, the SERS technique was used as a means to probe adsorption at metal interfaces both in electrochemical and gas-phase environments. This technique has proven useful in deducing the effects of interfacial structure and reactivity on the adsorption process. However, the sensitivity of the technique as well as its exceptional spectral selectivity has made SERS attractive for a broad range of analytical applications. SERS can be used for trace organic analysis and as a detection method in gas chromatography, liquid chromatography, and thin layer chromatography. Electrochemical SERS and SERS of chemically modified surfaces have been used to detect aromatic compounds and chlorinated hydrocarbons, organic contaminants of environmental concern, in the ppm concentration range.

There are many applications in which detection of particular chemical species or analytes is desirable, as for example, hydrocarbons that may be present in ground water, toxic vapors in industrial environments, explosives, metal ions, narcotics, toxic anions, and chemical warfare agents.

However, Raman scattering as a result of excitation of the optical elements of the sensor can obfuscate and/or interfere with detection of Raman scattering due to excitation of the species of interest. Therefore, a need exists for a SERS sensor that minimizes or eliminates Raman scattering due to excitation of the optical elements of the sensor.

SUMMARY OF THE INVENTION

The present invention provides a sensor for performing surface enhanced Raman spectroscopy (SERS) that employs a computer for implementing algorithms that minimize, or filter the influence of Raman scattering resulting from self-excitation of the optical elements of the sensor on the spectral output of the sensor attributable to Raman scattering of a species of interest.

A sensor performs surface enhanced Raman spectroscopy and employs a filter to minimize the effects of Raman scattering to self-excitation of the optical elements of the sensor. The sensor comprises: a) a sensor body having a throughbore; an optical energy source for generating an optical excitation signal; b) a surface enhanced Raman scattering structure that is mounted to the sensor body through which the optical excitation signal is directed for irradiating an analyte, whereupon the analyte generates primary Raman emissions in response to being irradiated by the optical excitation signal, and wherein the surface enhanced Raman scattering structure generates secondary Raman emissions when irradiated by the optical excitation signal; c) an optical detector for generating an output signal that represents the spectral characteristics of the primary and secondary Raman emissions in response to receiving the primary and second Raman emissions; and d) a processor for substantially filtering the secondary Raman emission from the primary Raman emissions and for generating an output signal representing the analyte.

These and other advantages of the invention will become more apparent upon review of the accompanying drawings and specification, including the claims.

BRIEF DESCRIPTION OF THE DRAWINGS

Throughout the several view, like elements are referenced using like references.

DESCRIPTION OF THE PREFERRED EMBODIMENT

Figure 1:
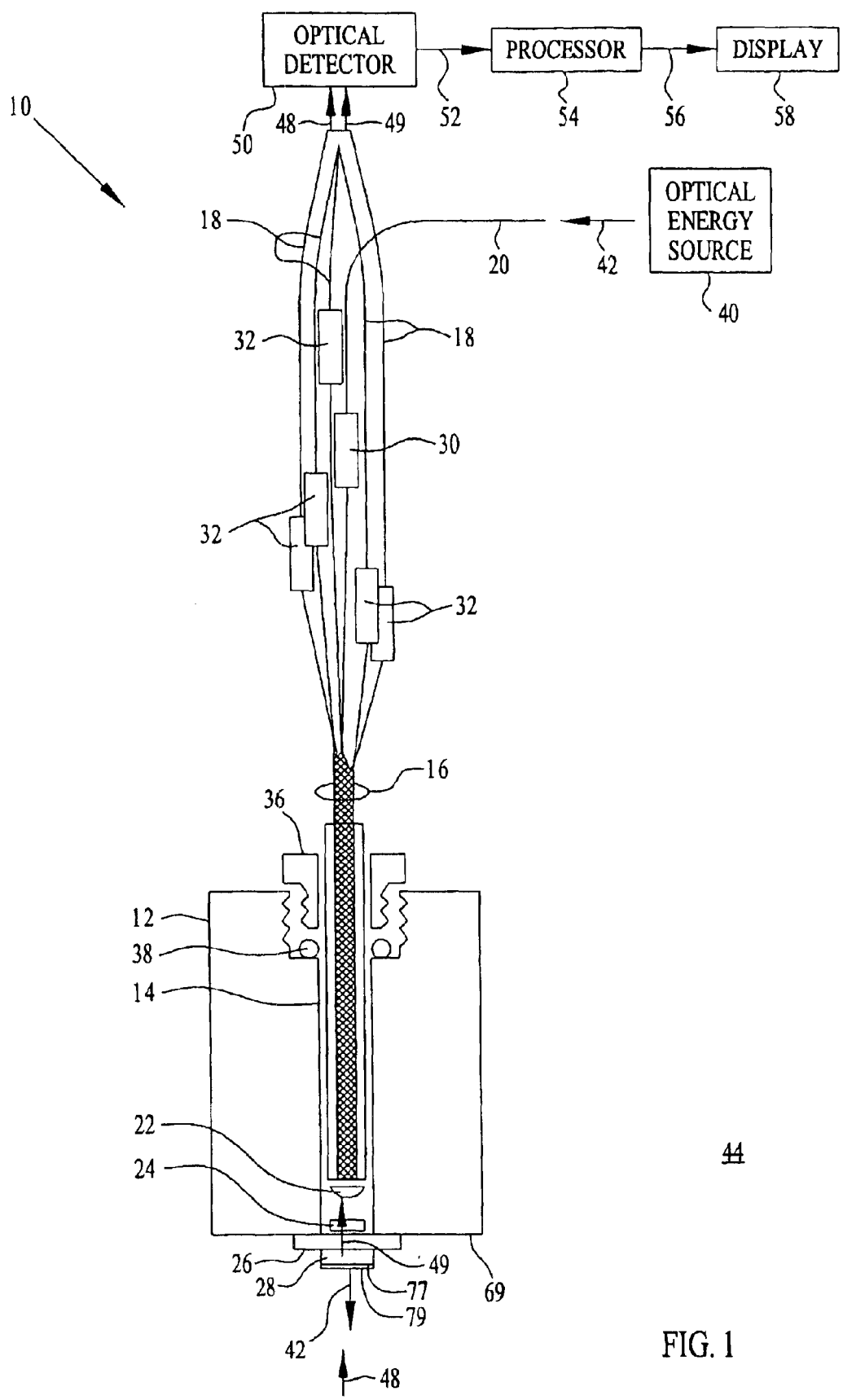
FIG. 1 illustrates a first embodiment of a fiber optic sensor for performing surface enhanced Raman spectroscopy that includes a SERS structure mounted to the window of the sensor.

Referring to FIG. 1, the present invention is directed to a sensor 10 for performing surface enhanced Raman spectroscopy. The sensor 10 includes a sensor body 12 having a throughbore 14 in which is positioned a fiber optic bundle 16 comprised of collection optical fibers 18, excitation optical fiber 20, collimating lens 22, focusing lens 24, window 26, and a Surface Enhanced Raman Spectroscopy (SERS) structure 28 that is described in commonly assigned U.S. patent application Ser. No. 09/593,675, filed 14 Jun. 2000, and entitled A METAL AND GLASS STRUCTURE FOR USE IN SURFACE ENHANCED RAMAN SPECTROSCOPY AND METHOD FOR FABRICATING SAME, incorporated herein by reference. Filter 30 is optically aligned and spliced to excitation optical fiber 20; and an optical filter 32 is optically aligned and spliced to each of collection optical fibers 18. Bushing 36 is threaded into sensor body 12 to secure the fiber optic bundle 16 within the bore 14 of the sensor body 12. An O-ring 38 may be interposed between bushing 36 and sensor body 12 to provide a watertight seal therebetween. Window 26 on which SERS structure 28 is bonded may be secured to sensor body 12 using adhesives, not shown, or by mechanical means, such as flanges or clamps.

In the operation of sensor 10, optical energy source 40 emits a light signal 42 that is directed to propagate through excitation optical fiber 20. Optical energy source 40 may be implemented as a krypton ion laser, near infrared (IR) diode laser, or Nd:YAG laser that generates light signals having wavelengths in the range, by way of example, from 647 to 1064 nm. Optical filter 30 is a bandpass filter that removes Raman emissions that may be excited within excitation optical fiber 20 by light signal 42. Light signal 42 is emitted from the polished end of excitation optical fiber 20 and then is collimated by lens 22 and focused by lens 26 onto the external surface 77 of the SERS structure 28 which is a SERS surface/liquid or SERS surface/vapor interface when sensor 10 is being utilized. Next, focused and collimated light signal 42 passes through window 26 and SERS structure 28 and is then emitted from sensor body 12 through the SERS structure 28 into the environment 44, which for example, may be a liquid or gas in which an analyte of interest may be present.

To stabilize the SERS response of surface 77, as well as to protect the metal films of the SERS structure 28 (described in detail in U.S. patent application Ser. No. 09/593,675, filed 14 Jun. 2000, and entitled A METAL AND GLASS STRUCTURE FOR USE IN SURFACE ENHANCED RAMAN SPECTROSCOPY AND METHOD FOR FABRICATING SAME) the metal films, made for example, of copper, silver, or gold, are coated. Thiols react with gold and silver substrates to form a self-assembled monolayer (SAM) coating 79 on the surface 77 of SERS structure 28. The SERS response of the thiol coating 79 may be used for calibration purposes. The particular thiol coating 79 is selected to have an affinity for a specific class of analytes of interest, where the analyte is the chemical that is desired to be detected by sensor 10. For example, a thiol coating 79 of 1-propanethiol has an affinity for aromatic and chlorinated solvents. A thiol coating 79 of dimethylaminoethanethiol hydrogen chloride has an affinity for negative ions such as nitrate and sulfate. A thiol coating 79 of an 18-crown-6 thiol derivative has an affinity for alkali metal ions such as sodium and potassium. Although particular examples of thiol coatings 79 have been presented herein, it is to be understood that they are presented by way of example only. The scope of the invention includes the use of other thiol coatings than those specifically identified above, as required to suit the needs of a particular application.

If an analyte of interest is present in environment 44, then the interaction of light signal 42 and the analyte in the presence of SERS structure 28 stimulates the generation of primary Raman emissions 48 that are transmitted through window 26, focusing lens 24, and collimating lens 22, and then enter collection optical fibers 18. Primary Raman emissions 48 due to the analyte(s) are directed by collection optical fibers 18 through long pass filters 32 which block the Rayleigh line, thereby preventing self-excitation of Raman emissions in collection optical fibers 18. The primary Raman emissions 48 are directed to optical detector 50 which detects the spectral components of signals 48. Secondary Raman emissions 49 are generally defined as Raman emissions that are generated as a result of irradiation of optical elements in the sensor 10. For example, secondary Raman emissions may be generated by irradiation of the thiol coating 79 of SERS structure 28 by light signal 42. Optical detector 50 generates signal 52 that represents the primary Raman emissions 48, particularly, the spectral components of primary Raman signals 48. Light signals 49 may interfere, obfuscate, or otherwise make detection of the Raman scattering resulting from stimulation of an analyte of interest in environment 44 more difficult. Therefore, it is desirable to try to eliminate or mitigate the influence of light signals 49 so as to more saliently distinguish signals 42.

Optical detector generally receives primary Raman light signals 48 and any secondary Raman light signals 49 resulting from excitation of the thiol coatings 79 by light signal 42. In response to receiving light signals 48 and 42, optical detector 50 generates an output signal 52 that represents the spectral characteristics of light signals 48 and 49. Processor 54 receives signal 52 and executes a computer program that substantially filters secondary Raman emissions associated with light signal 49 from primary Raman emissions associated with light signal 48. Processor 52 then generates an output signal 56 that represents an analyte of interest. One technique by which the secondary Raman emissions that characterize light signal 49 may be filtered from the primary Raman emissions that characterize light signal 48 is achieved whereby processor 54 creates a sample file that represents the combined spectral characteristics of light signals 48 and 49. Then, the computer program subtracts a reference file that represents the spectral characteristics of signal 49 from the sample file to create a data file that substantially represents only the spectral characteristics of primary Raman scattering signal 48. An example of a commercial computer program suitable for use in conjunction with the present invention by which representations, such as the reference file, of the spectral characteristics of one light signal may be subtracted, or filtered from the representations, such as the sample file, of the spectral characteristics of another light signal is known as Spectra Calc® by Galactic Industries, Inc.

Processor 54 may then employ additional software that uses the input file as an input to an algorithm which generates a value or "score" that may be entered into a look-up table, whereupon an output signal 56 is generated that represents the identity of one or more chemical species associated with that particular score. The chemical species associated with that score substantially have the spectral characteristics of the signal 48 when any of such chemical species is excited by light signal 42. The algorithm may be derived using a commercially available neural network program.

The reference file is created in a calibration process by exciting the thiol coating 79 on surface 77 with excitation light signal 42 in the absence of any analyte that could generate primary Raman scattering so that only light signals 49 are generated and directed to optical detector 50 via optical fibers 32. In response to detecting light signals 49, optical detector 50 generates an output signal 52 that substantially represents only the spectral characteristics of light signal 49. Processor 54 then creates and stores a reference file that represents the spectral characteristics of light signal 49.

Figure 2:
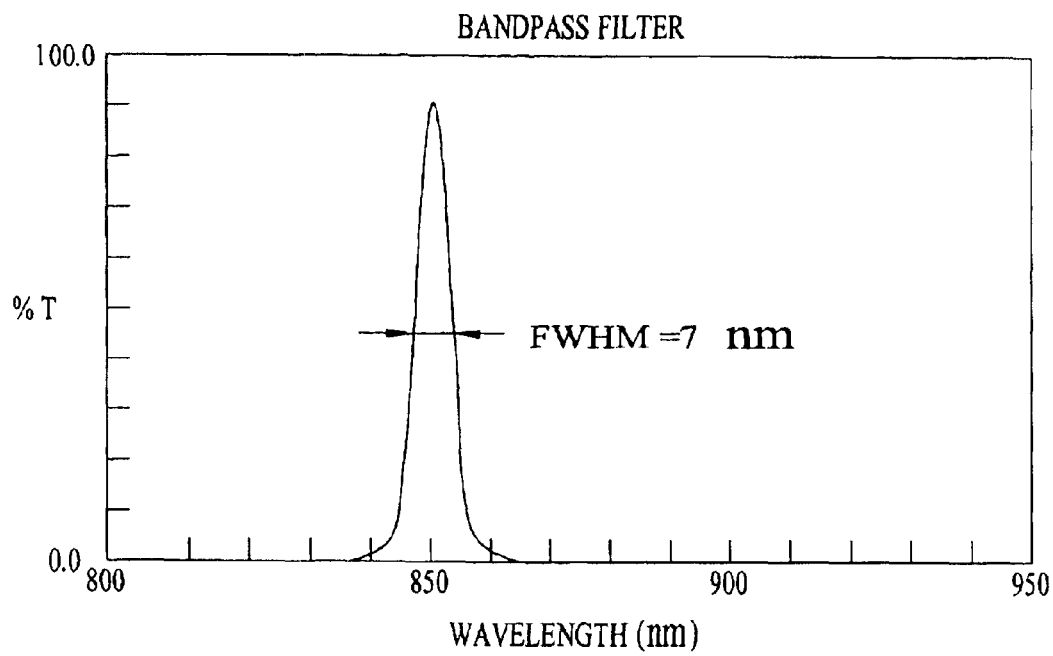
FIG. 2 shows transmission curves for the bandpass filter of FIG. 1 operating when the excitation light signal has a wavelength of 852 nm.
Figure 3:
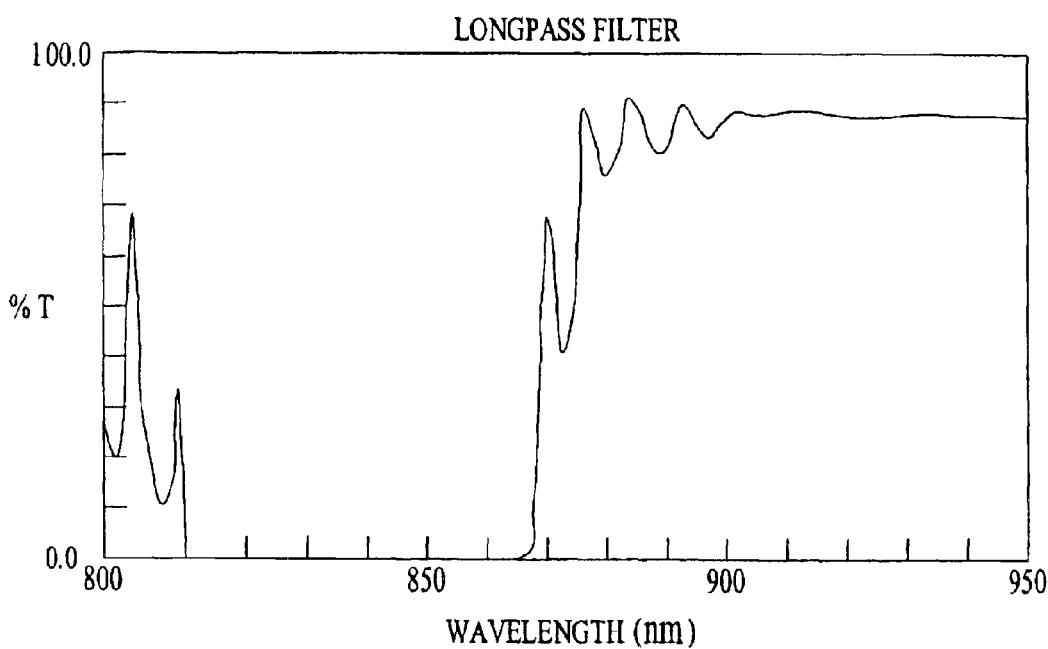
FIG. 3 shows transmission curves for the long pass filter of FIG. 1 operating when the excitation light signal has a wavelength of 852 nm.

By way of example, collection optical fibers 18 and 20, and filters 30 and 32 are available as a commercial package from Visionex, Inc., and may be selected for specific excitation wavelengths. FIGS. 2 and 3 shows transmission curves for the bandpass filter 30 and long pass filters 32, respectively, operating when excitation light signal 42 has a wavelength of 852 nm. FIG. 2 shows that the bandpass filter 30 has a very narrow bandpass centered about 850 nm and a full width, half maximum of value of 7 nm. FIG. 3 shows that the long pass filter 32 sharply passes light having wavelengths of about 868 nm or higher, but sharply attenuates light having shorter wavelengths than that.

Obviously, many modifications and variations of the present invention are possible in light of the above teachings. It is therefore to be understood that within the scope of the appended claims, the invention may be practiced otherwise than as specifically described.

We claim:

1. A sensor for performing surface enhanced Raman spectroscopy, comprising:
   a sensor body having a throughbore;
   an optical energy source for generating an optical excitation signal;
   a surface enhanced Raman scattering structure that is mounted to said sensor body through which said optical excitation signal is directed for irradiating an analyte, whereupon said analyte generates primary Raman emissions in response to being irradiated by said optical excitation signal, and wherein said surface enhanced Raman scattering structure generates secondary Raman emissions when irradiated by said optical excitation signal;
   an optical detector for generating an output signal that represents spectral characteristics of said primary and secondary Raman emissions in response to receiving said primary and secondary Raman emissions; and
   a processor for substantially filtering said secondary Raman emission from said primary Raman emissions and for generating an output signal representing said analyte.

2. The sensor of claim 1 which further includes a first optical fiber for directing said optical excitation signal through said SERS structure.

3. The sensor of claim 2 which further includes a bandpass filter for attenuating any self excited Raman emissions that may be stimulated by said optical excitation signal in said first optical fiber.

4. The sensor of claim 1 further including a second optical fiber for directing said primary and secondary Raman emissions to said optical detector.

5. The sensor of claim 1 further including a long pass filter for filtering optical signals having wavelengths less than a predetermined wavelength.

6. The sensor of claim 1 further including a display for presenting human readable indicia representing said analyte.

7. A sensor for performing surface enhanced Raman spectroscopy, comprising:
   a sensor body;
   an optical energy source for generating an optical excitation signal;
   a surface enhanced Raman scattering structure that is mounted to said sensor body through which said optical excitation signal is directed for irradiating an analyte, whereupon said analyte generates primary Raman emissions in response to being irradiated by said optical excitation signal, and wherein said surface enhanced Raman scattering structure generates secondary Raman emissions when irradiated by said optical excitation signal;
   an optical detector for generating an output signal that represents spectral characteristics of said primary and secondary Raman emissions in response to receiving said primary and second Raman emissions; and
   a processor for creating a sample file that represents said spectral characteristics of said primary and secondary Raman emissions, a reference file that represents said secondary Raman emissions, and a data file that represents the difference between said sample file and said reference file, and for generating an output signal that represents said analyte where said analyte has spectral characteristics represented by said data file.

8. A method for identifying an analyte using Raman spectroscopy, comprising the steps of:
   generating an excitation light signal;
   directing said excitation light signal through a SERS structure that is in contact with an analyte so that said analyte generates primary Raman spectral emissions when irradiated by said optical excitation signal, and wherein said SERS structure generates secondary Raman spectral emissions in response to being irradiated by said excitation light signal;
   generating an output signal representing said first and second Raman spectral emissions in response to detecting said first and second Raman spectral emissions;
   substantially filtering said secondary Raman emission from said primary Raman emissions to create a data file;
   identifying one or more candidate analytes characterized by said primary Raman emissions from said data file; and
   generating an output signal that represents said candidate analytes.

* * * * *